(12) United States Patent
Yoshimasa et al.

(10) Patent No.: US 8,476,483 B2
(45) Date of Patent: Jul. 2, 2013

(54) ANTIBACTERIAL SHEET AND ABSORBENT ARTICLE

(75) Inventors: Wataru Yoshimasa, Kanonji (JP); Satoru Sakaguchi, Kanonji (JP); Takayuki Hisanaka, Kanonji (JP)

(73) Assignee: Unicharm Corporation, Ehime (JP)

( * ) Notice: Subject to any disclaimer, the term of this patent is extended or adjusted under 35 U.S.C. 154(b) by 865 days.

(21) Appl. No.: 12/448,261

(22) PCT Filed: Nov. 30, 2007

(86) PCT No.: PCT/JP2007/073148
§ 371 (c)(1),
(2), (4) Date: Nov. 12, 2009

(87) PCT Pub. No.: WO2008/072487
PCT Pub. Date: Jun. 19, 2008

(65) Prior Publication Data
US 2010/0062031 A1 Mar. 11, 2010

(30) Foreign Application Priority Data
Dec. 13, 2006 (JP) ................. P2006-335936

(51) Int. Cl.
*A61F 13/15* (2006.01)
(52) U.S. Cl.
USPC .......................... 604/360; 424/411
(58) Field of Classification Search
USPC ............... 604/289, 290, 359, 360; 424/404, 424/405, 409, 411
See application file for complete search history.

(56) References Cited

U.S. PATENT DOCUMENTS

| | | | |
|---|---|---|---|
| 4,678,516 A | 7/1987 | Alderman et al. | |
| 4,695,464 A | 9/1987 | Alderman et al. | |
| 5,662,913 A * | 9/1997 | Capelli | 424/405 |
| 6,025,312 A | 2/2000 | Saito et al. | |

FOREIGN PATENT DOCUMENTS

| | | |
|---|---|---|
| CA | 2275302 A1 | 12/1997 |
| CN | 1348820 A | 5/2002 |
| EP | 0 177 893 A2 | 4/1986 |
| GB | 627797 A | 7/1946 |
| GB | 836477 A | 6/1960 |
| GB | 861379 A | 2/1961 |
| JP | 61-165337 | 7/1986 |
| JP | 05-103821 | 4/1993 |
| JP | 2000-070216 | 3/2000 |
| JP | 2000-505692 | 5/2000 |
| JP | 2001-039802 | 2/2001 |
| JP | 2005-198701 | 7/2005 |
| JP | 2006-043370 | 2/2006 |
| WO | WO2007/002025 | 1/1997 |
| WO | WO 98/26808 | 6/1998 |

OTHER PUBLICATIONS

JP 2001-039802 A to Yamazaki et al, English translation.*
Eurasian Office Action based on corresponding Eurasian Application No. 200900822/28 dated Oct. 25, 2010 and English translation (64pgs).
European Search Report based on corresponding European Application No. 07832845.7 dated Aug. 21, 2012 (3 pgs).
Australian Office Action based on corresponding Australian Application No. 2007330862 dated Aug. 29, 2012 (4 pgs).
Chinese Office Action based on corresponding Chinese Application No. 200780046177.3 dated May 18, 2012 and English translation (6 pgs).
Official Action based on corresponding Chinese Application No. 200780046177.3 dated Jan. 17, 2013 and English translation (6 pgs).
Official Action based on corresponding Indonesia Application No. W00200901611 dated Oct. 22, 2012 and English translation (4pgs).
Official Action based on corresponding Eurasian Application No. 200900822 dated Dec. 5, 2012 (3 pgs).

* cited by examiner

*Primary Examiner* — Melanie Hand

(74) *Attorney, Agent, or Firm* — Brinks Hofer Gilson & Lione

(57) ABSTRACT

Disclosed is an antibacterial sheet including an antibacterial composition and a sheet-like base member with the antibacterial composition attached thereto. In the antibacterial sheet, a composition including an antibacterial agent and a water-soluble thermoplastic polymer which is solid at a normal temperature and which dissolves in a body fluid is used as the antibacterial composition.

8 Claims, 3 Drawing Sheets

US 8,476,483 B2

ANTIBACTERIAL SHEET AND ABSORBENT ARTICLE

RELATED APPLICATIONS

The present application is a 35 U.S.C. §371 national stage filing of International Patent Application No. PCT/JP2007/073148, filed Nov. 30, 2007, to which priority is claimed under 35 U.S.C. §120 and through which priority is claimed under 35 U.S.C. §119 to Japanese Priority Patent Application No. 2006-335936, filed Dec. 13, 2006.

TECHNICAL FIELD

The present invention relates to an antibacterial sheet and an absorbent article using the antibacterial sheet.

BACKGROUND ART

In absorbent articles such as sanitary napkins, pantiliners and absorbent pads, bacteria in body fluid such as sweat, urine and menstrual blood may proliferate, which may cause skin sore or inflammation. Here, techniques for providing such an absorbent article with an antibacterial function have been known.

Specifically, there have been known uses of: fibers each having a surface directly coated with an antibacterial agent; a sheet coated with an antibacterial agent after the sheet is formed; and fibers made to contain an antibacterial agent by, for example, kneading the antibacterial agent (Patent Document 1: JP-A H5-103821). Furthermore, there has been known an absorbent article configured to completely kill unwanted bacteria in a binder binding pulp and a super absorbent polymer which form an absorber, by adding and mixing an antibacterial agent into the binder (Patent Document 2: JP-A 2005-198701). Polyvinyl alcohol is used as the binder.

DISCLOSURE OF THE INVENTION

In such an absorbent article, the antibacterial agent preferably exerts the action of completely killing unwanted bacteria in a body fluid while being in a wetted state due to absorption of the body fluid.

However, the conventional technique in Patent Document 2 has a problem that the antibacterial agent is not readily released from the polymer used as the binder. Specifically, polyvinyl alcohol is crystalline, and poorly-soluble in cold water, although soluble in hot water (at 75° C. or more). Hence, even when polyvinyl alcohol is brought into contact with a body fluid (at approximately 37° C.), the antibacterial agent mixed into the polyvinyl alcohol is hardly released, and cannot exert the effect. Similarly, the antibacterial agent is not readily eluted from (bleeds out of) the fiber in Patent Document 1 which contains the antibacterial agent. As a result, a sufficient antibacterial effect cannot be expected.

On the other hand, use of the fiber coated with an antibacterial agent directly may arouse concern about skin irritation due to the antibacterial agent, which is a chemical agent. In addition, there is another problem that the antibacterial agent exposed on the surface of the fiber is likely to lose its action before the absorption of a body fluid.

For this reason, an object of the present invention is to provide an antibacterial sheet and an absorbent article which are capable of effectively exerting antibacterial effects upon contact with a body fluid.

A first aspect of the present invention provides an antibacterial sheet including: an antibacterial composition; and a sheet-like base member with the antibacterial composition attached thereto. In the antibacterial sheet, the antibacterial composition includes: a water-soluble thermoplastic polymer which is solid at a normal temperature and which dissolves in a body fluid; and an antibacterial agent.

A second aspect of the present invention provides an absorbent article including the antibacterial sheet according to the above-described first aspect of the present invention.

A third aspect of the present invention provides an antibacterial composition including: a water-soluble thermoplastic polymer which is solid at a normal temperature and which dissolves in a body fluid; and an antibacterial agent.

BEST MODES FOR CARRYING OUT THE INVENTION

Figure 1:
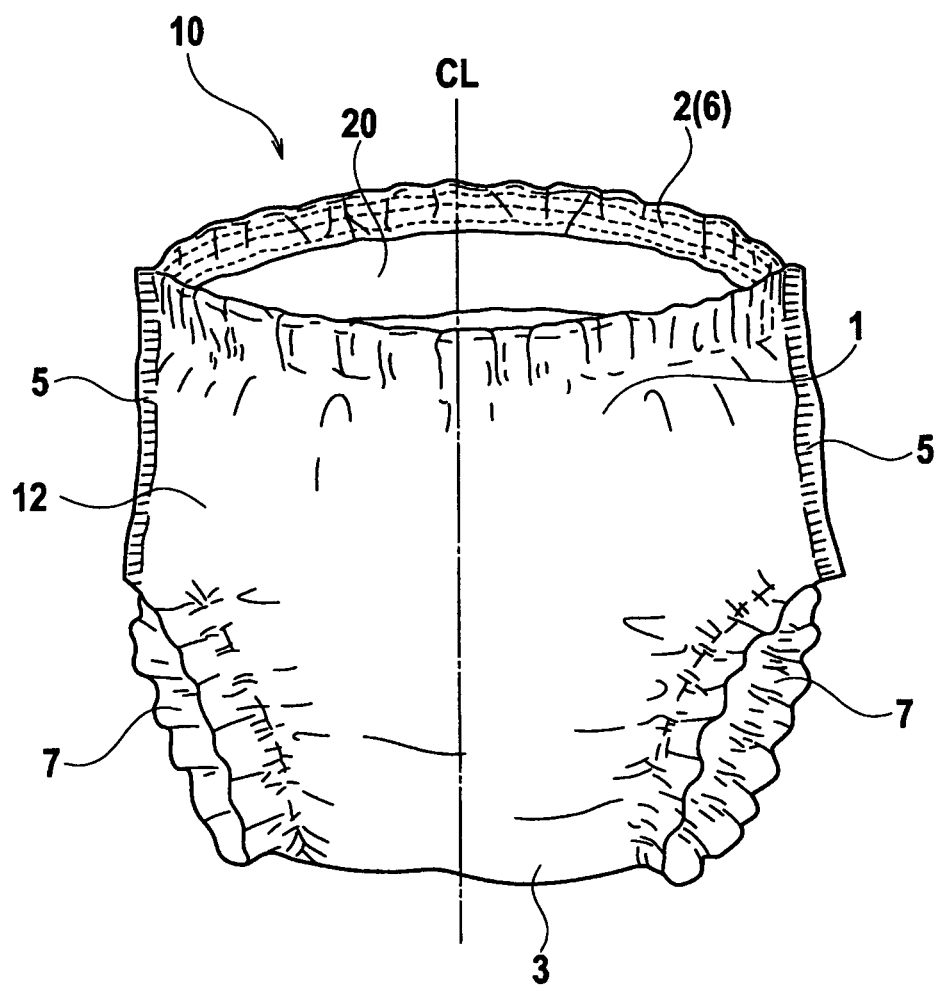
FIG. 1 is a perspective view showing an embodiment of a disposable diaper.

In an antibacterial sheet according to the present invention, a water-soluble thermoplastic polymer (hereinafter, also simply referred to as a "polymer") is used as a carrier of an antibacterial agent in an antibacterial composition attached to a sheet-like base member. The water-soluble thermoplastic polymer is solid at a normal temperature and dissolves in a body fluid. Thus, the polymer dissolves into a body fluid upon contact therewith. As a result, the antibacterial agent in the polymer is released, and thereby can exert an antibacterial effect. Until being in contact with a body fluid, the polymer remains solid. Thus, the antibacterial agent is held in the polymer and remains unreleased.

Hence, the present invention makes it possible to control the release of the antibacterial agent, and thereby the antibacterial action can be more effectively exerted with a small amount of antibacterial agent. This can prevent skin sore or the like, keeping the skin clean, and can provide an antibacterial sheet and an absorbent article which also provide comfortable wearing feeling.

The antibacterial sheet is a sheet including a sheet-like base member with an antibacterial composition attached thereto.

Herein, the "sheet" has no limitation on its width, length and thickness, and is a concept which includes, for example, a film, a tape, and the like.

The kind of the base member is not particularly limited, and any one of a synthetic resin sheet, a woven fabric, a non-woven fabric, a paper sheet, and the like can be used as the sheet-like base member. The kinds of a synthetic resin and a fiber are not limited, and various kinds of base members which are commonly used for an absorbent article or the like can be used. The base member may have any of a single-layer structure and a multi-layer structure. Furthermore, the base member may be formed of a hydrophilic material; alternatively, the base member may be formed of a hydrophobic material whose surface is provided with hydrophilicity through surfactant treatment. Meanwhile, as the base member, a porous film having pores formed by perforation, stretching, tentering, punching, or the like may be used. The porosity of such a porous film is preferably 10 to 60%, and the average diameter of the pores is preferably around 0.1 to 2 mm.

Typical examples include spunbonded polypropylene (PP) (for example: 1.9 dtex, a weight per unit area: 20 g/m$^2$), spunlaced polyethylene terephthalate (PET)/rayon/PET (for example: 1.7 dtex, weight per unit area: 25 g/m$^2$), a tissue containing pulp or rayon (for example: weight per unit area: 15 g/m$^2$). A non-woven fabric obtained by a through-air method or a point bond method or a non-woven fabric having an SMS three-layer structure (S: spunbonded non-woven fabric, M: melt-blown non-woven fabric or high-barrier material) may be used. Moreover, the base member may be one using a fiber having a core-sheath structure or a side-by-side structure of PE (polyethylene)/PP, PE/PET, or other combinations.

The antibacterial sheet may have a structure (layers) of a bonding layer, an adhesive layer, a water-repellent layer, or the like, as needed, in addition to the sheet-like base member structure.

The antibacterial composition includes a water-soluble thermoplastic polymer and an antibacterial agent. The polymer serves as a carrier for the antibacterial agent or as a binder for the non-woven fabric or the like. The antibacterial agent is preferably mixed and dispersed uniformly in the polymer.

The polymer is solid at a normal temperature and dissolves in a body fluid upon contact therewith. In other words, the polymer is solid (at a normal temperature) in a state where no body fluid is present, i.e., before contact with the body fluid.

The normal temperature represents a temperature at which an antibacterial sheet and an absorbent article are commonly used, and is, for example, room temperature (25° C.). In other words, a polymer having a solidifying temperature of 25° C. or more is preferably used as the polymer which is solid at a normal temperature.

It is not preferable that the polymer be liquid at a normal temperature, because, if so, the antibacterial agent may be released to the skin even in the absence of a body fluid, which may causes excessive irritation to the skin. Furthermore, it is not preferable that the polymer be liquid at a normal temperature, because, if so, such a polymer may give a tacky feeling which reduce wearing comfortableness, and because the antibacterial effect may be lost owing to the removal of the antibacterial agent from the sheet. This removal of the antibacterial agent occurs during production or before use of the product, because the antibacterial agent attaches to production equipment, a packaging material, a finger, or the like.

The body fluid is a generic term for fluids outside cells inside the bodies of animals, such as blood, lymph, and tissue fluid, and is a concept which includes fluids discharged from the body, such as sweat, urine, and menstrual blood.

The water-solubility of the polymer is evaluated according to its solubility in water at 37° C. A beaker containing 100 cc of water is heated with a water bath set at a constant temperature of 37° C. Into the beaker, 1 g of a polymer sample is added with stirring at a revolution speed of 700 rpm by using a stirrer. If a polymer dissolves completely 5 minutes after the addition, the polymer is termed as a water-soluble polymer, herein.

Since the polymer can dissolve in a body fluid, the polymer is eluted into the body fluid upon the contact with the body fluid. As a result, the antibacterial agent in the composition is released, and starts to exert the action. On the other hand, in a state where no body fluid is present, the antibacterial agent in the polymer is not released. This prevents the antibacterial agent from causing irritation on user's skin, and also prevents the loss of effect of the antibacterial agent before absorption of the body fluid. Furthermore, favorable indigenous bacteria, which reside in the skin, are not sterilized before the absorption of the body fluid.

In this way, the present invention makes it possible to control the release of the antibacterial agent.

Heat rash is a typical skin trouble. A study conducted by the inventors has revealed that *Staphylococcus epidermidis* on the skin grows excessively because of perspiration, and that this excessive growth is a factor causing heat rash. With the antibacterial sheet of the present invention, the polymer dissolves upon contact with sweat to release the antibacterial agent. Accordingly, bacteria in the sweat are completely killed instantaneously, and thus heat rash is prevented.

Moreover, as the polymer, a thermoplastic polymer, that is, a water-soluble thermoplastic polymer is selected, because such a polymer allows formation of a flexible coating while avoiding being cured by heat or the like in processing the antibacterial sheet.

Such a polymer is not particularly limited, as long as the polymer has the above-described characteristics. Specifically, polyethylene glycols (hereinafter also referred to as "PEG"s) and derivatives thereof can be used preferably.

The derivatives of PEGs include fatty acid esters of PEGs in which the terminals of PEGs are esterified, and polyoxyethylene alkyl ethers in which the terminals of PEGs are etherified. Examples of the fatty acid esters of PEGs include: polyethylene glycol dioleate, diethylene glycol distearate, polyethylene glycol distearate, diethylene glycol dilaurate, polyethylene glycol dilaurate, diethylene glycol stearate, polyethylene glycol palmitate, polyethylene glycol monooleate, polyethylene glycol monostearate, polyethylene glycol monolaurate, polyethylene glycol lanolin fatty acid ester, and the like. Examples of the polyoxyethylene alkyl ethers include polyoxyethylene octyl dodecyl ether, polyoxyethylene oleyl ether, polyoxyethylene stearyl ether, polyoxyethylene cetyl ether, polyoxyethylene cetostearyl ether, polyoxyethylene butyl ether, polyoxyethylene hexyl decyl ether, polyoxyethylene lauryl ether, and the like. Any of these derivatives can be used alone or in combination of two or more.

As PEGs which are solid at a normal temperature (25° C.) and which are water-soluble at 37° C., ones each having a molecular weight (a weight average molecular weight measured by the GPC method in terms of polyethylene standards, hereinafter the same) of 100 to 50000 are preferably used. The molecular weight is more preferably around 600 to 30000.

It is preferable to use multiple kinds of PEGs having molecular weights different from each other or derivatives thereof. The use of a PEG having a small molecular weight improves adhesion of the antibacterial composition to the base member, which can prevent removal of the antibacterial agent even when the sheet is subjected to pressure during wearing or to friction. This can also prevent the sheet from being hard and can provide flexibility thereto. On the other hand, the use of a PEG having a large molecular weight prevents a tacky feeling, thereby making it possible to prevent skin discomfort or irritation.

Such use of the multiple kinds of PEGs having molecular weights different from each other or the derivatives thereof is preferable, because solubility in a body fluid, flexibility and adhesion (fixation) to the base member can be achieved in a well-balanced manner.

Specifically, as a PEG (PEG-S) having a small molecular weight, a PEG having a molecular weight of 100 or more but less than 2000 is preferably used. As a PEG (PEG-L) having a large molecular weight, a PEG having a molecular weight of 2000 to 50000 inclusive is preferably used. As each of the PEG-S and the PEG-L, multiple kinds of PEGs having molecular weights different from each other can be used.

The mixing ratio of the PEG-S and the PEG-L is not particularly limited, partially because the mixing ratio depends on the molecular weight of each of the PEGs. For example, the weight ratio of PEG-S:PEG-L is preferably 1:9 to 9:1, more preferably 1:9 to 7:3, still more preferably 1:9 to 5:5, and further preferably 2:8 to 4:6.

As the antibacterial agent, any antibacterial agent can be used, as long as the antibacterial agent can suppress the growth of bacteria such as *Escherichia coli, Staphylococcus aureus, Staphylococcus epidermidis*, and ammonia producing bacteria. The antibacterial agent can be used in combination of two or more. Herein, the "antibacterial" represents a concept which includes partial sterilization, complete sterilization and bacteriostasis.

The followings are specific examples:
formaldehyde-releasing agents such as N,N',N''-tris(hydroxyethyl)hexahydro-s-triazine, 2-bromo-2-nitro-1,3-propanediol, 4,4-dimethyl oxazolidine, 1,3-di(hydroxymethyl)-5,5-dimethylhydantoin, tris (hydroxymethyl)nitromethane, 4-(2-nitrobutyl) morpholine, and 1,3-dimorpholino-2-nitro-2-ethylpropane;
halogen-containing compounds such as 1,3-dibromo-2,4-dicyanobutane, diiodomethyl-p-tolylsulfone, 2,3,5,6-tetrachloro-4-(methylsulfonyl)pyridine, and 2,4,5,6-tetrachloro isophthalonitrile;
iodopropagyl derivatives such as 4-chlorophenyl-3-iodopropagylformal, and 3-iodopropagylbutylcarbamate;
thiocyanate compounds such as 2-(4-thiocyanomethylthio)benzothiazole;
isothiazolinone derivatives such as 2-octyl-4-isothiazoline-3-one, 5-chloro-2-methyl-4-isothiazoline-3-one, 1,2-benzisothiazolone-3, and N-butyl-1,2-benzisothiazolone-3;
trihalomethylthio compounds such as N-(fluorodichloromethylthio)phtalimide, N,N-dimethyl-N'-(fluorodichloromethylthio)-N'-phenylsulfamide, and N-dichlorofluoromethylthio-N',N'-dimethyl-N-p-tolylsulfamide;
quaternary ammonium salts such as alkyl dimethyl benzyl ammonium chloride, dodecyl dimethyl benzyl ammonium chloride, benzethonium chloride, hexadecyl trimethyl ammonium bromide, didecyl dimethyl ammonium chloride, decyl isononyl dimethyl ammonium chloride, hexadecyl pyridinium chloride (cetyl pyridinium chloride), 4,4'-(tetramethylenedicarbonylamino)bis(1-decylpyridinium bromide), and N,N'-hexamethylenebis (4-carbamoyl-1-decyl pyridinium bromide);
biguanide compounds such as polyhexamethylene biguanide hydrochloride, chlorhexidine gluconate, and chlorhexidine hydrochloride;
aldehydes such as formaldehyde, 1,5-pentanedial (glutalaldehyde), and α-bromocinnamaldehyde;
phenols such as 3-methyl-4-chlorophenol, 4-chloro-3,5-dimethylphenol, and alkyl (methyl, ethyl, propyl, butyl) p-hydroxybenzoate;
benzimidazole derivatives such as 2-(4-thiazolyl)benzimidazole, and methyl 2-benzimidazolyl carbamate;
pyridine oxides such as sodium pyridine-2-thiol-1-oxide and zinc bis(2-pyridylthio-1-oxide);
carbanilides such as 3,4,4'-trichlorocarbanilide and 4,4-dichloro-3-(trifluoro methyl)carbanilide;
diphenyl ethers such as 2,4,4'-trichloro-2'-hydroxydiphenyl ether;
carboxylic acids such as sorbic acid, propionic acid, 10-undecylenic acid and benzoic acid; and
organometallic compounds such as 10,10'-oxybisphenoxyarsine.

Furthermore, antibacterial agents which can be used herein include:
kampo medicines which show antibacterial action, such as *artemisia capillaris* flower, fennel, *astragalus* root, coptis rhizome, phellodendron bark, *scutellaria* root, wormwood leaf, licorice root, apricot kernel, *cassia* bark, magnolia bark, *perilla* herb, peony root, cnidium rhizome, rhubarb, clove, peach kernel, and mutan bark;
natural antibacterial agents which are added to food, such as styrax extract, *Artemisia capillaris* Thunb. extract, Magnolia obovata extract, forsythia extract, pectin digests, protamine, polylysine, α-polylysine, ε-polylysine, citrus seed extract, ginger extract, tea extract, raw soybean extract, digest of red breadlike food made of wheat gluten (BENIFU), *Psoralea corylifolia* L. extract, moso bamboo extract, rice hull extract, lysozyme, pepper extract, and propolis; and
other natural antibacterial agents such as mustard extract, chitosan, and derivatives thereof.

Among the above-described antibacterial agents, a water-soluble antibacterial agent which is soluble in water is preferably used, because the water-soluble antibacterial agent can effectively exert its function upon contact with a body fluid.

Particularly preferable antibacterial agents are cationic surfactants which absorb *Staphylococcus epidermidis*, i.e., a plausible pathogen of heat rash, and which destroys the cell membranes of the bacteria. The examples of the cationic surfactant include cetylpyridinium chloride (CPC) and the like.

The amount of the antibacterial agent blended into the antibacterial composition is not particularly limited, and may be set as appropriate in accordance with the antibacterial activity of the antibacterial agent used, the application of the antibacterial sheet, or the like. The amount of the antibacterial agent attached to the sheet-like base member is preferably around 0.001 to 0.1 g/m$^2$, and more preferably around 0.005 to 0.05 g/m$^2$.

The antibacterial composition may contain any one or more additives or the like in addition to the above-described water-soluble polymer and the above-described antibacterial agent. Examples of such additional components include a colorant, a perfume, a deodorant, an antioxidant, an ultraviolet preventing agent, an antistatic agent, a pH adjuster, a lubricant, a dispersant, a softener, ahumectant, an anti-inflammatory agent, an antihistamine, and the like.

When the antibacterial composition contains, for example, a perfume and a deodorant, these agents effectively exert their effects upon contact with a body fluid as similar to the antibacterial agent, thereby making it possible to provide high deodorant and perfume effects.

Meanwhile, the composition may be a solvent-containing type which uses water, an organic solvent, or the like; however, a solventless type is preferable from the view point of the environmental concern and the elimination of the drying process.

The antibacterial composition is attached to the sheet-like base member. The attachment may be in such a state that, in a normal use, the antibacterial composition is not removed and remains on the base member.

The antibacterial composition may be attached continuously or discontinuously to surfaces (at least one surface) of the base member or the inside thereof, and may be attached not on the entire surface of the base member but on part thereof. The antibacterial composition can be attached in any pattern such as a film pattern, a particulate pattern, a lined pattern, a grid pattern, a dotted pattern, and a mesh pattern. In addition, when the base member has a multi-layer structure, the antibacterial composition may by attached to at least one surface of any one of layers included in the base member.

The attached amount of the antibacterial composition is not particularly limited; however, the attached amount is preferably around 0.05 to 10 $g/m^2$, and more preferably around 0.5 to 5 $g/m^2$, and further preferably around 1 to 3 $g/m^2$.

A method of attaching the antibacterial composition to the base member is not particularly limited, and, for example, the attachment is performed by coating the base member with the antibacterial composition. As a coater, a commonly-used coater, for example, a contact-type coater such as a slot coater, a roll coater, or a gravure coater, or a non-contact coater such as a spray or a spiral can be used.

Among those, the non-contact coater is preferably used, and the spray coater is particularly preferably used, because a thin film can be formed and because no influence is given to other processed portions.

For example, a preferable coating method is as follows. The antibacterial composition is heated to melt the water-soluble polymer which is solid at a normal temperature, and then the base member is coated with the antibacterial composition by spray coating. The heating temperature is not particularly limited, and may be set as appropriate in accordance with the melt temperature and the viscosity of the polymer. However, the heating is preferably performed at approximately 50 to 150° C., generally, and at approximately 60 to 100° C., normally.

The antibacterial sheet can be used in various applications. Examples of the applications include a packaging material of food or the like, a kitchen paper, a wiping sheet, a medical sheet such as a wound-covering pad, a disposable underwear, a toilet mat, and various absorbent articles.

In particular, the antibacterial sheet is preferably used in an absorbent article for absorbing a body fluid. Examples of the absorbent article include: a disposable diaper; a sanitary napkin, a pantiliner, a vaginal discharge sheet, and an incontinence pad, each of which is used while being attached to the inner surface of shorts; an absorbent pad which is used while being attached to the inner surface of a diaper cover; and the like.

An absorbent article generally includes: a front face sheet (a top sheet) which is in contact with the skin; a back face sheet (a back sheet) which is in contact with a surface of clothes; and an absorber (an absorbent core) located between these two sheets. As components of the absorbent article, various publicly-known materials are used, and the component materials of the absorbent article are not particularly limited.

Specifically, the front face sheet is liquid-permeable, and, as the front face sheet, a non-woven fabric formed of a hydrophilic fiber such as a rayon fiber, a pulp fiber, and a synthetic fiber, a porous plastic sheet, or the like can be used preferably. The back face sheet is liquid-impermeable, and, as the back face sheet, various plastic sheets such as polyethylene and polyvinyl alcohol can be used. The back face sheet may be air-permeable or air-impermeable. Each of the front face sheet and the back face sheet may have a multi-layer structure. For example, the back face sheet may have a structure in which a non-woven fabric is laminated on a plastic sheet. The absorber is formed of a laminated body of pulp or a laminated body of pulp and a super absorbent polymer.

In such an absorbent article, the antibacterial sheet can be used on the front face of the absorbent article or inside the absorber.

When used as the front face sheet, the antibacterial sheet may be used as part of the front face sheet. Here, the use of the antibacterial sheet as the front face sheet or as part of the front face sheet includes a case where the antibacterial sheet is pasted on the front face sheet. When used as part of the front face sheet, for example, in a disposable diaper, the antibacterial sheet is preferably disposed at the back part of the disposable diaper as a sweat absorbent sheet for heat rash prevention.

An antibacterial composition-attached surface of the antibacterial sheet used as the front face sheet may be located on the front-most surface which is on the skin side, or on the absorber side which is not in contact with the skin. When the antibacterial composition-attached surface is located on the absorber side, the body fluid diffuses into the sheet-like base member and reaches the antibacterial composition to dissolve the polymer. Thus, the function of the antibacterial agent is exerted.

Furthermore, in order to separate perspired sweat or excreted urine from the skin side, for example, the antibacterial sheet preferably has a hydrophobic skin-side surface and an inside part with hydrophilicity. Specifically, the antibacterial sheet is preferably formed of a non-woven fabric having a multi-layer structure provided with: a layer formed mainly of a hydrophobic fiber made mainly of polyethylene, polyethylene terephthalate, or polypropylene on the surface side; and a layer formed mainly of a hydrophilic fiber made of rayon, pulp, or the like inside the non-woven fabric.

Hereinafter, an embodiment in which an antibacterial sheet is applied to a disposable diaper as a sweat absorbent sheet will be described with reference to the drawings.

FIG. 1 is a perspective view showing the disposable diaper. The disposable diaper is an underpants-type diaper 10 which is formed bilaterally symmetrically about the axis center line.

The underpants-type diaper 10 includes a front waist region 1, a back waist region 2 and a crotch region 3. Here, right and left side edge sections 5 of the front waist region 1 and the back waist region 2 are jointed. Thus, a waist-opening 6 disposed on the upper side and a pair of right and left leg-openings 7 disposed on the lower side are formed.

Figure 2:
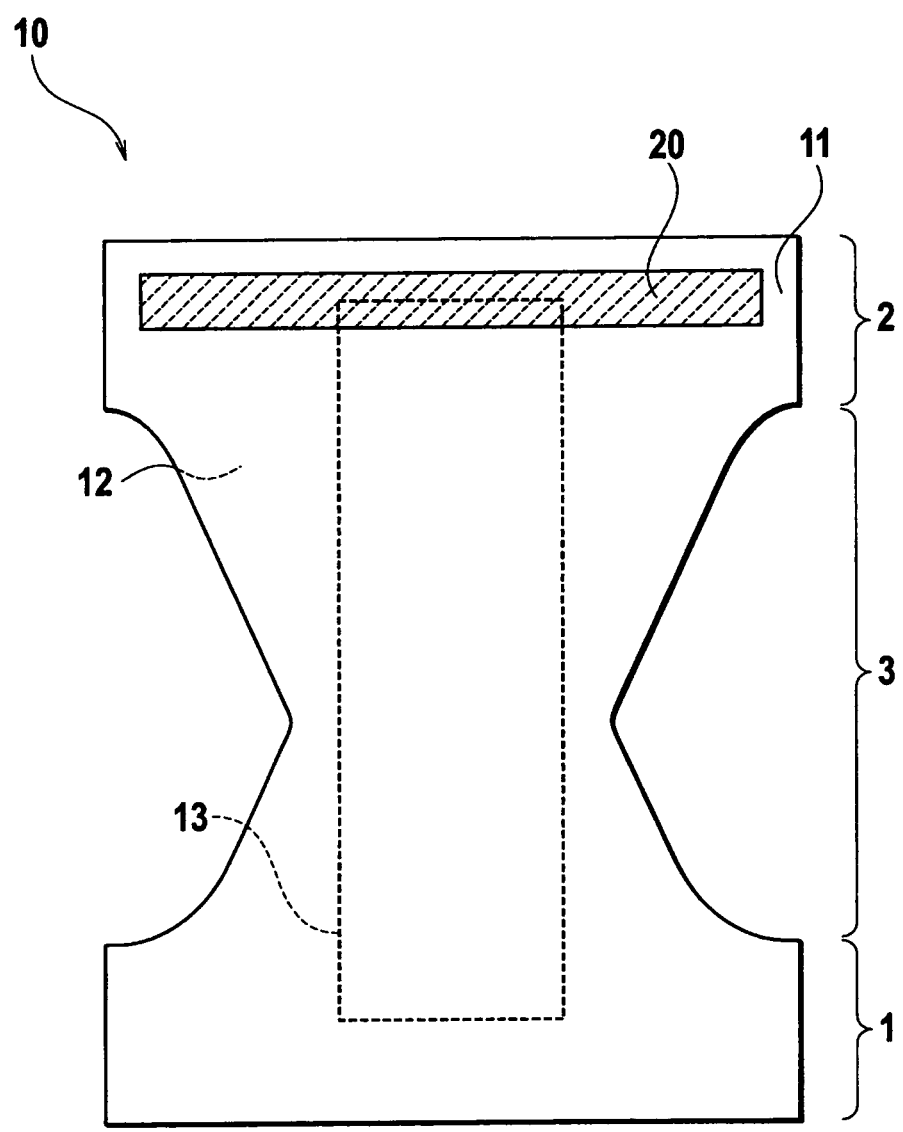
FIG. 2 is a plan view showing the spread diaper in FIG. 1.

FIG. 2 is a plan view showing the underpants-type diaper in FIG. 1 spread by separating the right and left side edge sections and viewed from the inner side of the diaper. As shown in FIG. 2, the underpants-type diaper 10 includes: a front face sheet 11 which is in contact with the skin; a back face sheet 12 which is in contact with a surface of clothes; and an absorber 13 located between these two sheets. On the back side of the front face sheet 11, an antibacterial sheet 20 is pasted while being away from the waist edge and the side edges.

Figure 3:
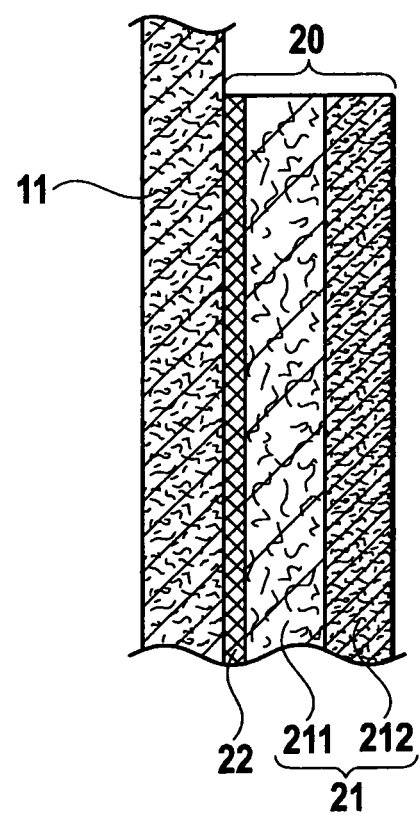
FIG. 3 is a cross-sectional view showing an embodiment of an antibacterial sheet.

As seen from a cross-section shown in FIG. 3, the antibacterial sheet 20 includes: a sheet-like base member 21 formed of a hydrophilic fiber layer 211 and a hydrophobic fiber layer 212; and an antibacterial composition layer 22 formed of an antibacterial composition. The antibacterial composition layer 22 is formed on the hydrophilic fiber layer 211 of the sheet-like base member 21. The antibacterial composition layer 22 side of the antibacterial sheet 20 is pasted on the front face sheet 11 with an adhesive layer (not shown).

EXAMPLES

Hereinafter, the present invention will be described in further details by way of Examples. However, the present invention is not limited to these examples.

<Production of Antibacterial Sheet>

An antibacterial composition (PEG:CPC=99:1) was obtained as follows. Specifically, as a water-soluble polymer for sheets A to C, PEG#600 and PEG#4000 (each number represents an approximate mean molecular weight, hereinafter the same) manufactured by NOF CORPORATION were used in a weight ratio of 3:7. To the PEGs, 1% by weight of cetylpyridiniumchloride (CPC, Wako Pure Chemical Industries, Ltd.) was added as an antibacterial agent to obtain the antibacterial composition.

An antibacterial composition (PVA:CPC=99:1) was obtained as follows. Specifically, as a polymer for sheets D and E, polyvinyl alcohol (PVA) (manufactured by Wako Pure Chemical Industries, Ltd., the polymerization degree: approximately 2000) was used. Similarly, 1% by weight of CPC was added to the PVA to obtain the antibacterial composition. This PVA is solid at a normal temperature and does not dissolve in water at 37° C.

As sheet-like base members, spunlaced polyethylene terephthalate/rayon/polyethylene terephthalate members (weight per unit area: 38 g/m², 285 mm×60 mm) were used.

Each of the sheets A to E was obtained as follows. Specifically, the corresponding one of the above-described antibacterial compositions was heated to 80° C. to melt the polymer, and the sheet-like base member was coated with the antibacterial composition by using a non-contact Q coater (manufactured by DYNATECH Co., Ltd.) at a speed of 100 m/minute so as to achieve the corresponding coating amount shown in Table 1.

As a sheet F, a kneaded-type antibacterial sheet (which is a spun sheet obtained by mixing 1% by weight of an inorganic antibacterial agent "ZEOMIC" manufactured by SINANEN ZEOMIC CO., LTD into polypropylene "NOVATEC-PP" manufactured by Japan Polypropylene Corporation, and by forming the spun sheet from the mixture by a spunbond method) was used. The production was carried out, so that the sheet F had a weight per unit area of 38 g/m² and the degree of fineness of 2 dtex.

TABLE 1

| | | STRUCTURE OF SHEET | | | | | |
|---|---|---|---|---|---|---|---|
| | | Sheet A | Sheet B | Sheet C | Sheet D | Sheet E | Sheet F |
| Proportion in antibacterial composition | PEG #600 | | 30 | | | | Kneaded-type antibacterial sheet |
| | PEG #4000 | | 69 | | | | |
| | PVA | | | | 99 | | |
| | CPC | | 1 | | | 1 | |
| Application amount (g/m²) | | 0.5 | 1.0 | 1.5 | 1.0 | 2.0 | |

Examples and Comparative Examples

Antibacterial Action Evaluation Test

By use of each of the above-described antibacterial sheets, the growth suppression effect on *Staphylococcus epidermidis* (Strain: NBRC12993) was evaluated by the following method.

The above-described test strain was cultured by using a blood agar medium at 35° C. for 20 hours. The obtained test bacteria were suspended in sterile saline so as to achieve a McFarland turbidity of 0.5 (approximately $10^8$ CFU/ml). Thus, test liquid containing the bacteria was prepared. The test liquid containing the bacteria was added into 1/10 Mueller Hinton broth (MHB) medium to achieve approximately $10^4$ CFU/ml, and then 0.5 ml of the medium containing the test liquid was dispensed into each well of a 24-well flat-bottom microplate (Well diameter: 16 mm, manufactured by IWAKI CO., LTD, for cell culture).

Each test sample (which is obtained by cutting one of the above-described antibacterial sheets into a circular shape with a diameter of 15 mm) was soaked into the liquid surface part in one of the wells, and left in stationary culture at 35° C. As a control for growth, a well into which no test sample was soaked was provided.

Immediately after each test sample was soaked, and after 2-, 4-, 8-, and 24-hour culture, the culture medium in each of the wells was taken out and the viable cell count was determined.

A case where the cell count became in the order of $10^{-1}$ (CFU/mL) (below the detection limit) within 24 hours was graded as effective.

Table 2 shows the results.

TABLE 2

GROWTH-SUPPRESSION EFFECT ON Staphylococcus epidermidis

|  | Antibacterial sheet | Culture time (hour) | | | | |
|---|---|---|---|---|---|---|
|  |  | Immediately after | 2 | 4 | 8 | 24 |
| Example 1 | Sheet A | $1.2 \times 10^4$ | $4.0 \times 10^1$ | $<2.0 \times 10^1$ | $<2.0 \times 10^1$ | $<2.0 \times 10^1$ |
| Example 2 | Sheet B | $1.1 \times 10^4$ | $<2.0 \times 10^1$ | $<2.0 \times 10^1$ | $<2.0 \times 10^1$ | $<2.0 \times 10^1$ |
| Example 3 | Sheet C | $7.8 \times 10^3$ | $<2.0 \times 10^1$ | $<2.0 \times 10^1$ | $<2.0 \times 10^1$ | $<2.0 \times 10^1$ |
| Comparative Example 1 | Sheet D | $1.2 \times 10^4$ | $1.0 \times 10^4$ | $7.1 \times 10^3$ | $5.9 \times 10^4$ | $2.2 \times 10^6$ |
| Comparative Example 2 | Sheet E | $1.2 \times 10^4$ | $5.2 \times 10^3$ | $2.4 \times 10^3$ | $3.0 \times 10^4$ | $5.1 \times 10^5$ |
| Comparative Example 3 | Sheet F | $1.2 \times 10^4$ | $3.4 \times 10^3$ | $2.5 \times 10^3$ | $6.9 \times 10^4$ | $1.1 \times 10^7$ |
| Control for growth |  | $1.2 \times 10^4$ | $1.2 \times 10^4$ | $8.0 \times 10^3$ | $7.2 \times 10^4$ | $1.6 \times 10^7$ |

As seen in Table 2, the antibacterial sheets A to C of Examples showed sufficient antibacterial effects. In contrast, the sheets D to F of Comparative Examples did not show sufficient antibacterial effects. This is plausibly because the antibacterial agents were not sufficiently released.

<Production of Underpants-Type Diaper with Antibacterial Sheet>

An antibacterial composition which is the same as that of the sheet B in Table 1 was prepared, and then spunlaced PET/rayon/PET was coated with the antibacterial composition in the same manner as described above. Thus, an antibacterial sheet (dimensions: 55 mm×285 mm, coating amount: 1 g/m$^2$) was produced.

The obtained antibacterial sheet was pasted onto back part of an underpants-type diaper (Moony Man manufactured by Unicharm Corporation) with an adhesive coated thereonto (see FIGS. 1 and 2). Here, the antibacterial composition layer was located on the front face sheet side. Thus, each underpants-type diaper of the Example 4 with the antibacterial sheet was produced.

In Comparative Example 4, diapers with no antibacterial sheet pasted thereonto were used. In Comparative Example 5, diapers with the above-described sheet F (kneaded-type antibacterial sheet, dimensions: 55 mm×285 mm) pasted thereonto were used.

Example and Comparative Examples

Heat Rash Suppression Effect Test

Wearing test of each of the diapers was performed as follows.

As subjects, 50 infants (a half is male and the other half is female) who were around 24-month old (and used L sized-diapers) and who had already experienced heat rash in the year of this experience were selected. Test period was from Aug. 1 to 7, 2006, i.e., the period during which heat rash is most likely to develop. During the period, diapers were used as usual. The development of heat rash on the back of each of the infants near the part where the antibacterial sheet was pasted was visually observed by the mother. Heat rash which required care such as drug application was particularly graded as "anxious heat rash." On average, 25 diapers were used during the period. Criteria for overall evaluation are as follows.

A: Both of the incidences of heat rash and of anxious heat rash are 20% or less.

B: Both of the incidences of heat rash and of anxious heat rash are more than 20% but 40% or less.

C: Any one of or both of the incidences of heat rash and of anxious heat rash exceed 40%.

Table 3 shows all the obtained results.

TABLE 3

|  |  | Wearing test | | |
|---|---|---|---|---|
|  |  | Example 4 | Comparative Example 4 | Comparative Example 5 |
| Types of antibacterial sheet used |  | Sheet B | None | Sheet F (kneaded-type antibacterial sheet) |
| Evaluation result | Incidence of heat rash (%) | 18 | 56 | 46 |
|  | Incidence of anxious heat rash (%) | 11 | 42 | 36 |
|  | Overall evaluation | A | C | C |

As shown in Table 3, in the case where the diapers of Example were worn, developments of heat rash were suppressed when compared with these in Comparative Examples.

The disclosure in the present application is related to the subject matter described in Japanese Patent Application No. 2006-335936 filed on Dec. 13, 2006, and all disclosed contents therein are incorporated herein by reference.

It should be noted that, in addition to the above description, various adjustments or modifications can be made on the above-described embodiment without departing from the novel and advantageous characteristics of the present invention. Accordingly, it is intended that all of such adjustments and modifications are included in the attached CLAIMS.

The invention claimed is:

1. An antibacterial sheet comprising:
   an antibacterial; and
   a sheet-like base member to which the antibacterial composition is attached, wherein
   the antibacterial composition includes:
   a water-soluble thermoplastic polymer which is solid at a normal temperature and which dissolves in a body fluid; and an antibacterial agent,
   wherein the water-soluble thermoplastic polymer comprises a first derivative of a polyethylene glycol having a molecular weight of from 100-2000 and a second derivative of a polyethylene glycol having a molecular weight of 2000 to 5000, and a ratio of the first polyethylene to the second polyethylene is 1:9 to 7:3.

2. The antibacterial sheet according to claim 1, wherein the water-soluble thermoplastic polymer comprises a plurality of kinds of derivatives of polyethylene glycols having molecular weights different from each other or derivatives thereof.

3. The antibacterial sheet according to claim 1, wherein the antibacterial agent is a water-soluble antibacterial agent.

4. The antibacterial sheet according to claim 2, wherein the antibacterial agent is a water-soluble antibacterial agent.

5. An absorbent article comprising the antibacterial sheet according to claim 1.

6. An absorbent article comprising the antibacterial sheet according to claim 2.

7. An absorbent article comprising the antibacterial sheet according to claim 3.

8. An absorbent article comprising the antibacterial sheet according to claim 4.

* * * * *

UNITED STATES PATENT AND TRADEMARK OFFICE
CERTIFICATE OF CORRECTION

PATENT NO. : 8,476,483 B2
APPLICATION NO. : 12/448261
DATED : July 2, 2013
INVENTOR(S) : Yoshimasa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1028 days.

Signed and Sealed this
Eighth Day of September, 2015

Michelle K. Lee
*Director of the United States Patent and Trademark Office*